United States Patent [19]
Goto

[11] Patent Number: 5,238,026
[45] Date of Patent: Aug. 24, 1993

[54] LIQUID OUTFLOW CONTROL UNIT

[75] Inventor: Nobuo Goto, Tokyo, Japan

[73] Assignee: Chisso Corporation, Osaka, Japan

[21] Appl. No.: 551,536

[22] Filed: Jul. 12, 1990

[30] Foreign Application Priority Data

Nov. 14, 1989 [JP] Japan .................. 1-296353
May 23, 1990 [JP] Japan .................. 2-133218

[51] Int. Cl.$^5$ .................. F16L 1/04; F15D 1/00
[52] U.S. Cl. .................. 138/30; 138/40; 138/42; 138/157; 604/246
[58] Field of Search .................. 138/40, 42, 43, 44, 138/156, 157, 162, 166, 171, 151, 30; 604/65, 93, 246, 247, 251, 264, 280

[56] References Cited

U.S. PATENT DOCUMENTS

| | | | |
|---|---|---|---|
| 1,231,897 | 7/1917 | Jenkins .................. | 138/137 |
| 1,714,373 | 5/1929 | Johnson .................. | 138/44 |
| 1,964,300 | 6/1934 | Perry et al. .................. | 138/43 |
| 2,013,242 | 9/1935 | Johns .................. | 138/162 |
| 2,236,084 | 3/1941 | Brown .................. | 138/43 |
| 2,434,008 | 1/1948 | Osborn .................. | 138/44 |
| 2,662,541 | 12/1953 | Noon .................. | 138/44 |
| 3,086,559 | 4/1963 | Grenell .................. | 138/157 |
| 3,556,155 | 1/1971 | McWilliams et al. .................. | 138/43 |
| 3,730,227 | 5/1973 | Roberts et al. .................. | 138/40 |
| 4,318,400 | 3/1982 | Peery et al. . | |
| 4,626,243 | 12/1986 | Singh et al. .................. | 138/44 |
| 4,759,387 | 7/1988 | Arendt .................. | 138/42 |

FOREIGN PATENT DOCUMENTS

56-102252 8/1981 Japan .
61-51901 11/1986 Japan .
62-11464 1/1987 Japan .
62-11465 1/1987 Japan .

*Primary Examiner*—James E. Bryant, III
*Attorney, Agent, or Firm*—Lowe, Price, LeBlanc & Becker

[57] ABSTRACT

A liquid outflow control unit used in an instrument for injecting a liquid such as a liquid medicine into a human body. It includes a plurality of separate partial members, at least one of which has a groove on a joined face thereof to form a small path through which a liquid passes. A liquid enters one end of the groove and goes out of an exit which fluid communicates with the other end of the groove. The liquid flowing out of the exit is injected into the human body via a connection tube and a needle.

4 Claims, 7 Drawing Sheets

LIQUID OUTFLOW CONTROL UNIT

BACKGROUND OF THE INVENTION

1. Field of the Invention

The present invention relates to a liquid outflow control unit capable of controlling the flow rate of the injected liquid and used in a continuous liquid injector or the like for sequentially injecting into a desirable portion of a human body a liquid such as a liquid medicine accommodated within a liquid accommodating portion.

2. Description of the Related Art

In one of conventional methods of continuously injecting a liquid such as a liquid medicine into a human body, a liquid accommodated in an injector is manually or automatically supplied into the body through a needle or a catheter. In another method, a liquid in an instillator is naturally or automatically supplied into the body.

Such continuous injection of the liquid takes a few minutes or a few hours. During that time, a needle or the like is connected continuously to a syringe or the like, and this may cause pain to the patient or limit his or her actions during the injection. It may also be necessary for the operator, who may be a doctor or a nurse, to hold a syringe or check the amount of liquid given by an intravenous drip injection, making the injection procedure a troublesome task.

Accordingly, a small-sized easy-to-handle continuous liquid medicine injector (or catheter) which does not confine the actions of a patient or an operator has been proposed (for example, in Japanese Patent Laid-Open No 56-102252 and its corresponding U.S. Pat. No. 4,318,400, Japanese Patent Publication No. 61-51901 and Japanese Patent Laid-Open Nos. 62-11464 and 62-11465).

All of these conventional continuous liquid medicine injectors therein incorporate a balloon or a bag made of an elastic material. An inlet from which a liquid medicine is put into the balloon is provided in one end of the balloon, and an outlet from which the liquid medicine is forced out of the balloon is provided in the other end of the balloon. The inlet is provided with a check valve which allows the liquid medicine to flow into the balloon but does not permit it to flow out of the balloon. In such arrangement, the liquid medicine accommodated in the balloon is forced out of its outlet due to the contraction of the balloon against the human body through an instrument such as a needle inserted into the body.

However, all of these continuous liquid medicine injectors involve the problem that the flow of liquid medicine cannot be controlled sufficiently in the outlet. This has been a big obstacle to practical use of these injectors.

The outflow control of a liquid medicine in Japanese Patent Laid-Open No. 56-102252 is provided by a very thin flow control element provided in a fluid path (mouth) which fluid communicates between the inside and outside of the balloon. The flow control element includes a somewhat short linear pipe. A change in the flow is considered to be performed by changing the length and inner diameter of the pipe although they are not specifically described. However, it is considered to be virtually impossible to increase the length of the flow control element sufficiently because it is incorporated in the flow path and also to extremely reduce the inner diameter from a standpoint of manufacture. Thus, although a liquid medicine is required to be supplied in very small amounts to the human body for a long time depending on the kind of the medicine, the flow control element cannot sufficiently satisfy such requirement.

More specifically, in Japanese Patent Publication No. 61-51901, the flow of liquid medicine is controlled by suitably changing the diameter of through holes formed in the wall of the tube-like body on which the balloon is mounted or by employing a diaphragm which varies the area of the inner diameter of the outlet in the tube-like body in accordance with the inner pressure of the balloon. However, control of the diameter of the through hole formed in the tube wall does not ensure sufficient control of the flow rate due to the thinness of the tube wall. Also, the required diaphragm is difficult to manufacture and hence unsuitable for mass production, and its use is, therefore, not practical.

Furthermore, in the injector proposed in Japanese Patent Laid-Open No. 62-11464, control of the flow of liquid medicine is provided by varying the diameter of a thin tube (thin hole) formed so as to extend axially of the tube wall of a catheter. However, the formation of a thin axial hole in the thin catheter is difficult in itself, making precise control of the flow rate more difficult.

Furthermore, the injector proposed in Japanese Patent Laid-Open No. 62-11465 incorporates therein a liquid flow regulating valve in the liquid outlet, and flow control is provided by controlling the restricting ratio of the flow regulating valve. However, precise control is also difficult in this injector.

An object of the present invention is to provide a liquid outflow control unit which has a simple structure and which ensures precise control of the outflow of liquid.

SUMMARY OF THE INVENTION

According to the present invention, a liquid outflow control unit comprises a plurality of partial members of a synthetic resin to which the control unit is divided along the direction of flow of a liquid, at least one of the partial members having a groove on a joined face thereof to form a part of a small flow control path having one end which fluid communicates with a liquid inlet and the other end which fluid communicates with a liquid outlet.

In the present invention, the small flow control path is preferably composed of a groove provided in one flat surface of one member and a flat surface of the other member joined to the flat surface of the one member. Alternatively, both the members each may include a groove.

In the present invention, liquid leakage prevention means which includes a combination of a rib and a groove is preferably formed around the small flow control path.

If a rubber-like elastic film (balloon or bladder) as liquid accommodating and pressurizing means is provided so as to cover the outer periphery of the liquid outflow control unit according to the present invention, a communication hole which fluid communicates with the outer surface of the liquid outflow control unit is preferably formed on a part of the side of the liquid inlet in the small flow control path.

According to the present invention, a method of manufacturing a liquid outflow control unit comprises the steps of forming from a synthetic resin a plurality of partial members to which the control unit is divided along the direction of flow of a liquid, at least one of the partial members having a groove on a joined face thereof to form a part of a small flow control small path, and joining those partial members together closely on their joined faces.

In the inventive manufacturing method, the partial members are preferably formed using the injection molding. While the junction is preferably formed using ultrasonic adhesion.

The liquid outflow control unit having the above structure according to the present invention is easily manufactured by forming partial members of a synthetic resin using injection molding or the like and joining them together to thereby ensure mass production and stabilized quality. Since the small flow control path is formed by the joined surfaces of the partial members, the small path may take a proper form, for example, of being straight of course, crooked or zigzag. Control of the flow of liquid is provided very easily by setting the inner diameter and length of the small path to corresponding predetermined ones.

DETAILED DESCRIPTION OF THE PREFERRED EMBODIMENTS

An embodiment of the present invention will be described below with reference to the drawings.

Figure 1:
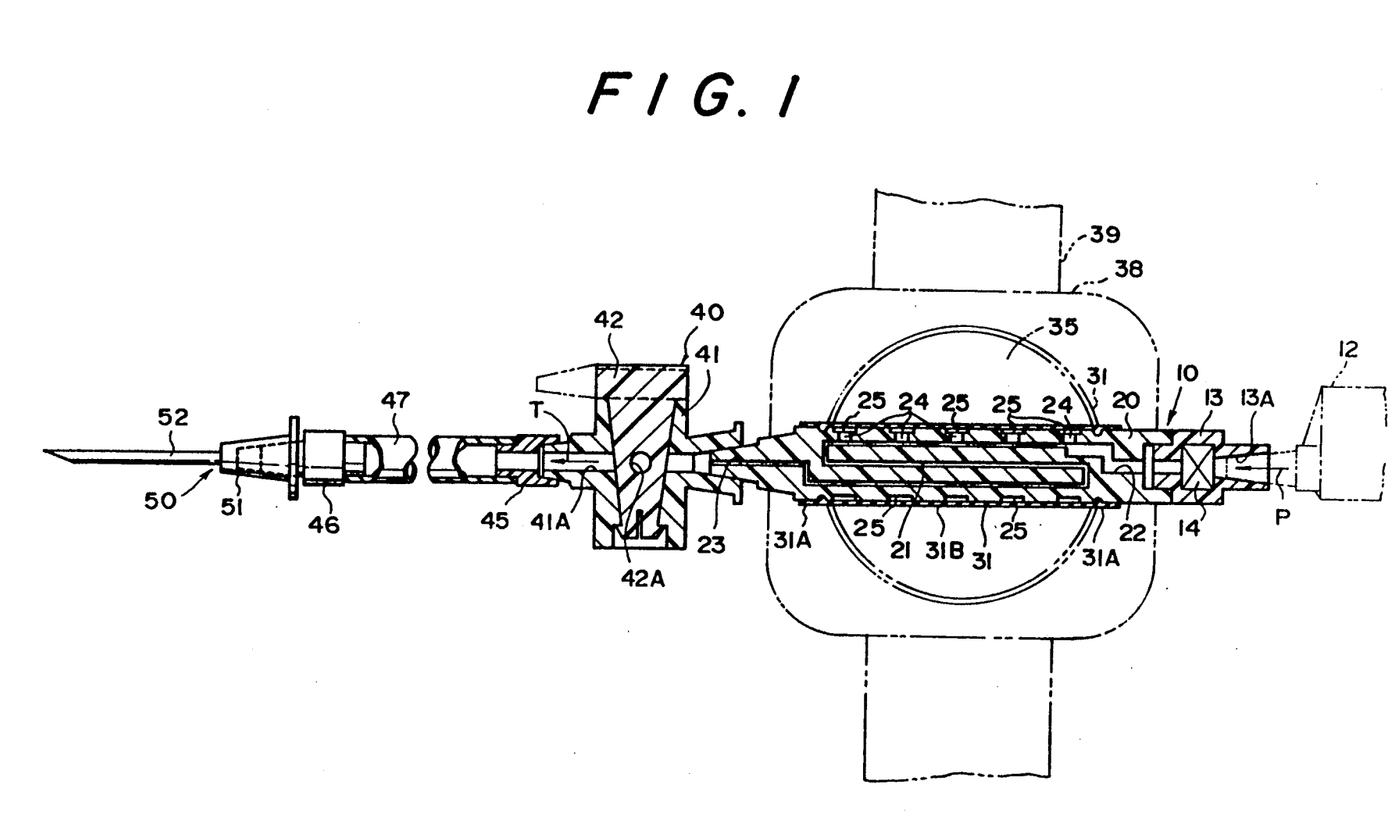
FIG. 1 is a cross-sectional view of one embodiment of a liquid outflow control unit according to the present invention applied to a continuous liquid injector.
Figure 2A:
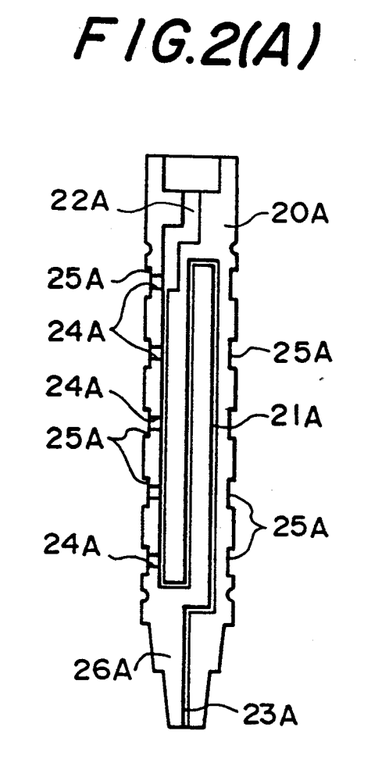
FIGS. 2(A) and (B) each are a plan view of a partial member used in the liquid outflow control unit of FIG. 1.
Figure 2B:
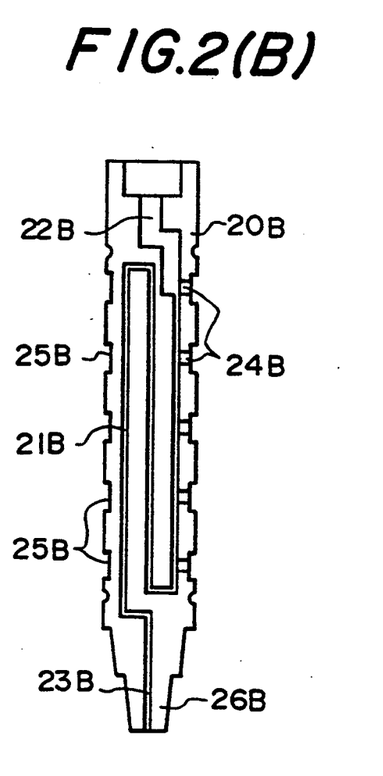
Figure 3:
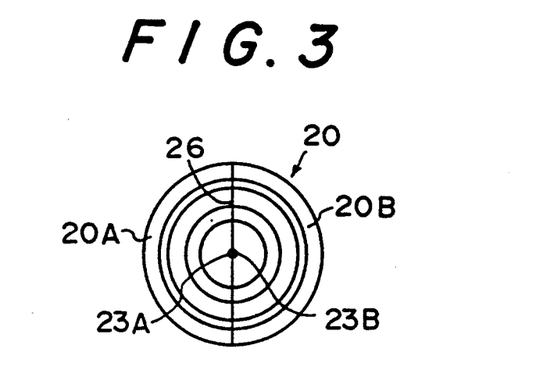
FIG. 3 is an enlarged side view of the joined partial member of FIG. 2.

FIGS. 1-3 shows one embodiment of a liquid outflow control unit according to the present invention applied to a continuous liquid injector.

In FIG. 1 which shows the overall structure of the embodiment, the continuous liquid injector 10 in the particular embodiment includes a substantially cylindrical liquid outflow control unit 20 made of a synthetic resin. The control unit is preferably made of a transparent or translucent material from the viewpoint of affording visibility of the interior thereof.

Provided at one end (the right-hand end as viewed in FIG. 1) of the control unit 20 is a liquid receiving portion 13 on which a syringe 12 serving as a liquid supply means can be mounted. Fixed in the liquid receiving portion 13 is a liquid outflow prevention means 14 for preventing the liquid, which has been injected into the control unit 20 from the syringe 12, from flowing out of the liquid receiving portion 13. This prevention means 14 may be a check valve which permits the flow of the liquid only in the direction of arrow P or a one-way cock which can open/close a flow passage 13A in the liquid receiving portion 13. Any suitable check valve or one-way cock available commercially may be used.

Provided within the liquid outflow control unit 20 in FIG. 2 is a small flow control path 21 or 21A which has a larger liquid inlet 22 at its right-hand end, in fluid communication with the liquid receiving portion 13, than its other end, namely, the left-hand end which includes a liquid outlet which constitutes an end of the small path and which has the same diameter as the small path. As shown, the small path 21 is formed zigzag to ensure a predetermined length. The small path 21 is, for example, several 10 $\mu$m to several 100 $\mu$m in diameter. By proper selection of the length and diameter of the small path, the flow rate of liquid flowing through the small path 21 is controlled.

A plurality of communication holes 24 which fluidly communicate with the outer surface of the liquid flow control unit 20 are formed in part of the liquid receiving portion 22 side of the small flow control path 21. Formed at the opening ends of the communication holes 24 on the control unit 20 are peripheral grooves 25 which fluidly communicate with the communication holes 24 to thereby facilitate the outflow and inflow of a liquid through the communication path 24.

FIGS. 2 and 3 illustrate the partial members of the liquid outflow control unit 20 and the joined members.

The liquid outflow control unit 20 is divided into a plurality of substantially equal partial members (two partial members 20A, 20B in the particular embodiments) in the direction of flow of the liquid or in the direction of arrow P in FIG. 1. These partial members 20A and 20B are separately formed of a synthetic resin by injection molding, for example. The synthetic resin includes a silicone resin, acryl, polycarbonate (PC), polyethylene (PE), polypropylene (PP), polyacetal (POM), polyamide (PA), flouroresin, bakelite, or any other thermoplastic or thermosetting resin. The material is preferably thermoplastic, suitable for injection molding, stable in a liquid and slightly transparent; for example, a polycarbonate.

Since the partial members 20A and 20B are formed symmetrical with reference to a joined face 26 for both the members, both the members will be described together by giving reference characters A and B at corresponding points of the members.

The partial members 20A and 20B have grooves 21A and 21B to form the small zigzag flow control path 21. They also have grooves 22A, 22B and 23A, 23B at one end and the other end of the grooves 21A and 21B to form liquid inlet and outlet 22 and 23, respectively. Furthermore, the partial members 20A and 20B have grooves 24A, 24B and 25A, 25B to form communication holes 24 and peripheral grooves 25, respectively.

As shown in FIG. 3, the partial members 20A and 20B are joined together such that their symmetrical patterns face and coincide on the joined face 26 and the joined faces 26A and 26B of the partial members 20A and 20B are joined by proper means, which preferably includes ultrasonic adhesion or may be other means such as bonding if inflow of an adhesive into the small path 21, for example, is prevented effectively.

In FIG. 1, a cylindrical rubber-like elastic membrane 31 is mounted on the control unit 20 in such a manner as to cover all the communication holes 24 in the control unit 20. The rubber-like elastic membrane 31 is fixedly attached to the outer periphery of the control unit 20 in an air-tight manner at two end portions 31A thereof, an intermediate portion 31B thereof being isolatable from the outer periphery of the control unit 20. The rubber-like elastic membrane 31 is preferably made of an elastic material which is sufficiently wear-resistant and tough and not readily damaged by external force. In particular, a transparent or translucent material is preferably employed. Suitable materials of the elastic membrane 31 include a silicone rubber and a latex rubber which are available commercially.

The rubber-like elastic membrane 31 is inflatable with the liquid which flows thereinto through the communication holes 24, as shown by the dot-line in FIG. 1. The inflated membrane 31 constitutes a liquid pressurizing means. The interior of the inflated membrane 31 and that of the control unit 20 constitute a liquid accommodating portion 35.

Detachably provided at the outer end portion, at the left side in FIG. 1, of the liquid outflow control unit 20 is a cock 40 which serves as an opening/closing means. The cock 40 includes a body 41 with a flow passage 41A formed therein, the body 41 being attached to the other end of the control unit 20 so as to be in fluid communication with the medicine outlet 23, and a knob 42 with a communication hole 42A which can communicate with the flow passage 41A formed therein, the knob 42 being pivotally provided in the body 41.

In consequence, the flow passage 41A can be blocked or made to communicate with the communication hole 42A by pivoting the knob 42. In the illustrations of FIG. 1, the communication hole 42A is disposed perpendicular to the flow passage 41A to block it. Turning of the knob 42 through 90 degrees from the state illustrated opens the flow passage 41A.

A needle 50 which is an instrument inserted into the human body is detachably mounted on the body 41 of the cock 40 through an elastic connecting tube 47 having connectors 45 and 46 at its ends. The needle 50, available commercially, includes a mounting portion 51 which can be mounted on one connector 46 of connection tube 47, and a needle 52 attached in the mounting portion 51.

In FIG. 1, a transparent cover 38, which covers a rubber-like elastic membrane 31 inflated in the form of a sphere, is mounted, if necessary. The cover 38 has a band 39 through which the cover 38 is mounted on the arm or the like of a patient. The cover 38 has the functions of protecting the rubber-like elastic membrane 31 in an inflated state and of fastening the injector onto the patient.

Next, the operation of the particular embodiment will be described.

First, the cock 40, as the opening/closing means, is mounted on one end of the control unit 20 of the continuous liquid injector 10, and the knob 42 of the cock 40 is operated as illustrated in FIG. 1 to close it. In this state, the syringe 12, which is a liquid supply means, is inserted into the liquid receiving portion 13 of the control unit 20, and a predetermined amount of liquid accommodated within the syringe 12 is forced out of it in the direction of arrow P.

The liquid is forced into the liquid inlet 22 through the liquid outflow prevention means 14. At that time, since the cock 40 mounted on the liquid outlet 23 side of the control unit 20 is in a closed state, the outflow of the liquid from the liquid outlet 23 is prevented. This causes the liquid to flow into the rubber-like elastic membrane 31 through the inlet 22 in the control unit 20 from the communication holes 24 formed in the small path 21, inflating the elastic membrane 31 in the form of a sphere. At that time, the contracting force of the elastic membrane 31 which is the reaction force caused by the inflation makes the rubber-like elastic membrane 31 serve as a pressurizing means which applies a predetermined amount of pressure to the liquid. At the same time, the interior of the control unit 20 and that of the inflated elastic membrane 31 constitute the liquid accommodating portion 35.

Further, the liquid filling in the rubber-like elastic membrane 31 is prevented from flowing back out of the liquid receiving portion 13 by the action of the liquid outflow prevention means 14 provided in the liquid receiving portion 13.

If it is required to prevent air from entering the control unit 20 and the rubber-like elastic membrane 31, the same type of liquid or physiological salt solution may be injected in the control unit 20 beforehand. Alternatively, the control unit 20 may be made upright with the liquid receiving portion 13 located up after the injection of the liquid. In this way, bubbles in the rubber-like elastic membrane 31 and the control unit 20 float up in the liquid receiving portion 13 of the control unit 20, so that the air is readily discharged through a tube vent (not shown) inserted into the liquid receiving portion 13 by opening the liquid outflow prevention means 14.

After a predetermined amount of liquid has been accommodated in the continuous liquid injector 10 in the manner described above, the needle 50, which is an instrument mounted on the human body, is mounted on the cock 40 through the connection tube 45 when required. This needle 50 is then inserted into the human body, thereby completing the preparation of injection of liquid into the human body.

When the needle 50 is inserted into the human body, air is vented by causing small amount of liquid to flow out of the needle 50, if necessary.

After the insertion of the needle 50 into the body, the flow passage 41A is opened by turning the knob 42 of the cock 40 to thereby make the hole 42A communicate with the flow passage 41A. This causes the liquid, accommodated in the liquid accommodating portion 35 and pressurized by the rubber-like elastic membrane 31 as pressurizing means, to flow into the small path 21 in the liquid outflow control unit 20 via the peripheral grooves 25 and communication holes 24. Thereafter, the liquid in the liquid outflow control unit 20 flows into the flow passage 41A of the cock 40 at a certain flow rate, i.e., in an amount determined by the inner diameter and length of the small path 21. The liquid flows through the flow passage 41A in the direction of arrow T, then into the human body (not shown) through the connection tube 47 and the needle 50. At that time, since the flow liquid outflow control unit 20, the flow of the liquid lasts for a predetermined period of time in spite of the pressure applied to the liquid by the inflated rubber-like elastic membrane 31.

The time during which the flow of the liquid lasts is determined by the amount of liquid injected, its viscosity, the elasticity of the rubber-like elastic membrane 31, the inner diameter and length of the small path 21 in the liquid outflow control unit 20, the pressure in the human body into which the liquid is to be injected, and so on. In practice, the details are determined by measuring the time required for a certain type of liquid to be forced out of each continuous individual liquid injector 10.

This embodiment has the following advantages.

The liquid outflow control unit 20 employs the small path 21 which has an accurate inner diameter formed by using an accurately worked mold. Thus, controlling of the flow rate of liquid with high accuracy is ensured by suitably setting the inner diameter and length of the path 21. Also, setting of the inner diameter and length of the small path 21 is possible by working the mold accurately. In consequence, easy mass production is attained, and the manufacturer cost of the continuous liquid injector 10 can be reduced.

Since the small path 21 can be formed long in a zigzag manner, the diameter of the small path 21 can be enlarged as its length is increased in the control of the same flow to thereby cause no problems such as clogging of the path.

Furthermore, the embodiment of the continuous liquid injector 10 has both the functions of accommodating and pressurizing/injecting the liquid. In consequence, it is small in size and has a simple structure. It also ensures easy handling of the injector. It does not therefore limit the actions of a patient, and alleviates the operator's task and time during which the operator is restricted. Furthermore, a provision of the liquid outflow prevention means 14 in the liquid receiving portion 13 and the hermetical sealing structure of the overall continuous liquid injector 10 ensure that no air enters into the injector 10 until the rubber-like elastic membrane 31 is completely contracted once air has been vented out of it.

Furthermore, since the use of the rubber-like elastic membrane 31 which is served as a pressurizing means renders the structure of the injector simple, making the overall injector small in size and light in weight.

The present invention is not limited to the above-described embodiment, but various modifications are available within the scope of the present invention in which the object of the present invention is achieved. In modifications of the present invention to be described below, the same reference numeral is used to denote a component of the modifications identical or corresponding to that of the embodiment and duplicate description of the component will be omitted or made briefly.

Figure 4:
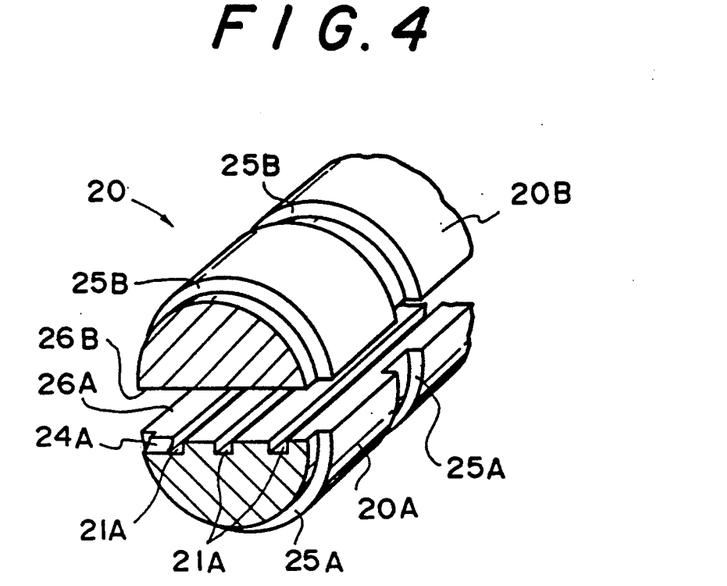
FIGS. 4 and 5 each are an enlarged exploded perspective view of the essential portion of a modification of the particular embodiment.

As shown in FIG. 4, grooves 21A may be provided on only one of the joined faces 26A and 26B of the partial members 20A and 20B (the joined face 26A of the partial member 20A in the particular embodiment) in order to form the small path 21 in the liquid outflow control unit 20. In this case, the groove 24A for the communication holes 24 may be provided at only one partial member 20A, while the joined face 26B of the other partial member 20B is formed flat. By such formation, one joined face, for example, 26B of the partial members 20A and 20B is flat, so that both the members 20A and 20B are easily aligned and joined rapidly.

Figure 5:
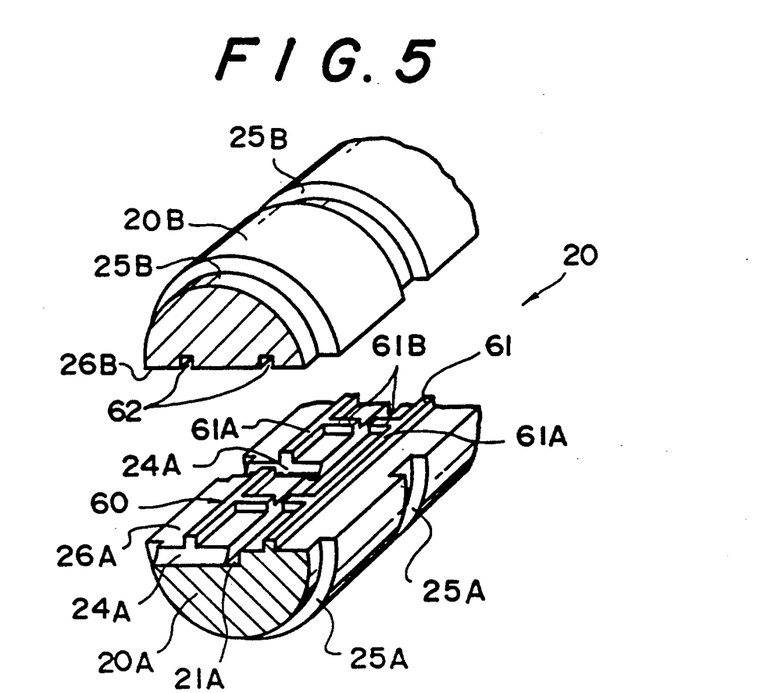

As shown in FIG. 5, like the embodiment of FIG. 4, liquid leakage prevention means 60 may be provided on each side of the small path 21 or the groove 21A in only the partial member 20A. The liquid leakage prevention means 30 includes a rib 61 provided on the side of one partial member 20A and a recess 62 provided on the other partial member 20B so as to be substantially complementary in shape to the rib 61.

The rib 61 includes a pair of longitudinal subribs 61A one provided on each side of the groove 21A and extending in the direction of flow of a liquid in order to prevent radial leakage of the medicine and a plurality of transverse subribs 61B provided between the longitudinal subribs 61A and between the grooves 24A to form the respective communication holes 24 except at the grooves 21A in order to prevent leakage of a liquid in the direction of flow of the liquid.

A change in the flow of the liquid due to leakage of the liquid out of the small path 21 through a possible small opening produced at the joined face 26 is prevented effectively by the above structure.

While in the particular modification, only one groove 21A is illustrated as being provided for clarity, the groove 21A may be formed zigzag so as to form three groove portions in the middle portion of the control unit 20 as shown in FIG. 1 or FIG. 4, of course. While in that case, the rib 61 and groove 62 are provided so as to prevent the leakage of the medicine from each groove 21A, the longitudinal subribs 61A between adjacent grooves 21A may be formed as a common single one. Conversely, a rib 61 and a groove 62 may be provided on the partial members 20B and 20A, respectively. Alternatively, no grooves may be provided on one partial member while only a rib may be provided on only the other partial member. Alternatively, both the partial members each may have a rib so as to reduce the joined area to eliminate a possible small opening between both the members. Only one groove 21A may be provided as one path groove, as shown, depending on the flow amount of the liquid. It is not necessarily zigzag. In summary, since the control of the flow amount of the liquid is determined by the cross-sectional area of the groove 21A orthogonal to the axis of groove 21A and the length of the groove, the cross-sectional area and length of the groove may be determined in manufacturing when required.

Figure 6:
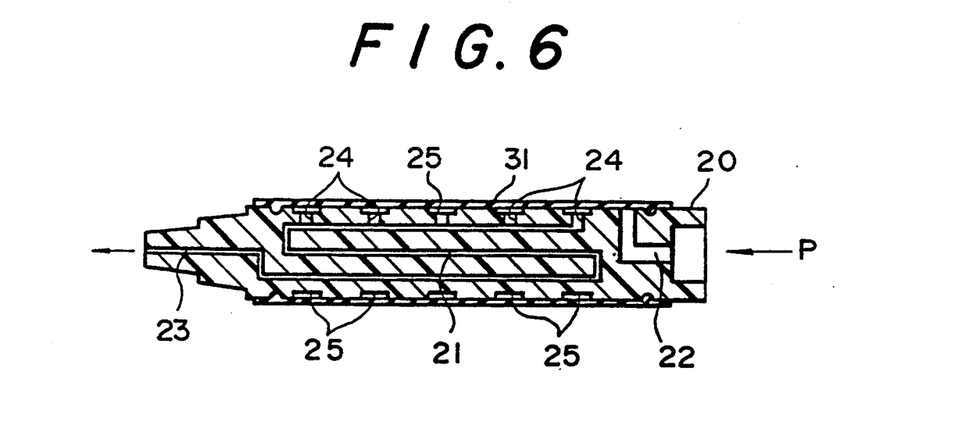
FIGS. 6 to 9 each are a cross-sectional view of a further embodiment of the present invention.

As shown in FIG. 6, the liquid receiving inlet 22 may not directly be connected to the flow control small path 21 and communicates with the small path 21 via the outer periphery of the liquid flow control unit 20 and the rubber-like elastic membrane 31 and through the peripheral grooves 25 and communication holes 24. By such structure, the same effects as those produced by the first embodiment are obtained.

In the particular embodiment of FIG. 6, the communication holes 24 each substantially constitute a liquid inlet for the small path 21.

The pressurizing means is not limited to the rubber-like elastic membrane 31 and other pressurizing means may be applicable.

Figure 7:
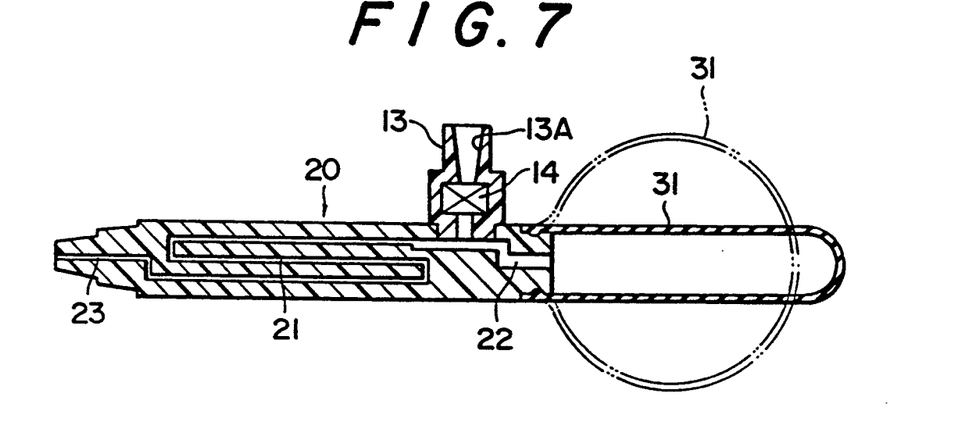
Figure 8:
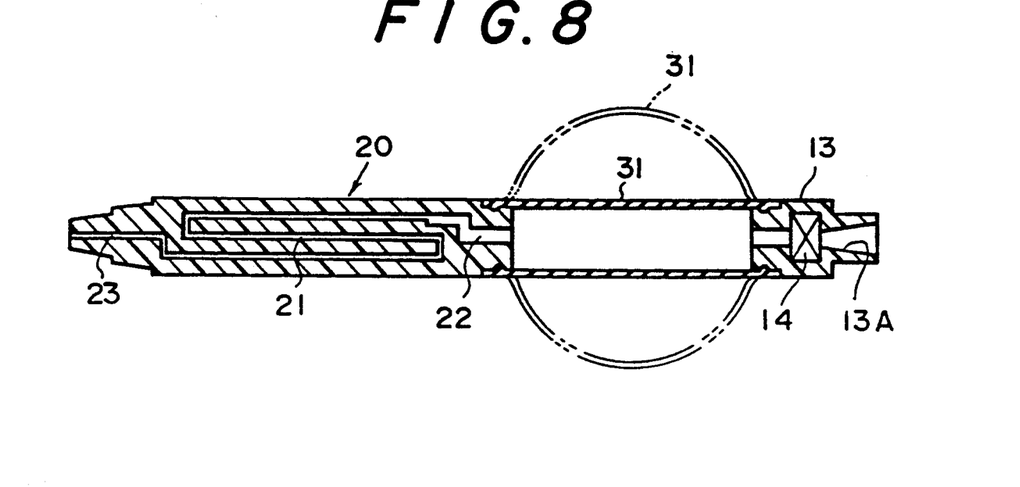

The position where the rubber-like elastic membrane 31 is attached to the liquid outflow control unit 20 is not limited to a position in the middle portion of the control unit 20. It may be at one end of the control unit 20, as shown in FIG. 7. In this case, the liquid receiving portion 13 is attached to the other end of the elastic membrane 31. No peripheral grooves and communication holes are formed on the control unit 20. In FIG. 8, of course, the other side of the elastic membrane 31 may be closed to form a balloon-like rubber-like elastic membrane 31 while the liquid medicine receiving portion 13 may diverge from the middle portion of the control unit 20 such that the path 13A communicates with the small path 21.

Means for adhering the partial members 20A and 20B of the control unit 20 each other is not limited to the aforementioned ultrasonic adhesion or bond, but can be employed as shown in FIGS. 9 to 13, in which the partial members 20A, 20B made of synthetic resin are under the operation of a insert resin-molding by means of injection molding or the like.

The partial members 20A, 20B shown in the embodiment of FIGS. 9 to 13 are of the members only for controlling the outflow amount of the liquid. A groove 21A having the shape of character V is formed on a joined face 26A of one partial member 20A, while on a joined face 26B of the other partial member 20B no grooves are formed. The small flow control path 21 consisted of the groove 21A and the joined face 26B has a cross sectional configuration of a equilateral triangle or a right angled triangle, in which one edge is set at the length of e.g., several 10 μm to several 100 μm and the control path 21 is a straight path having no bend portions.

Figure 9:
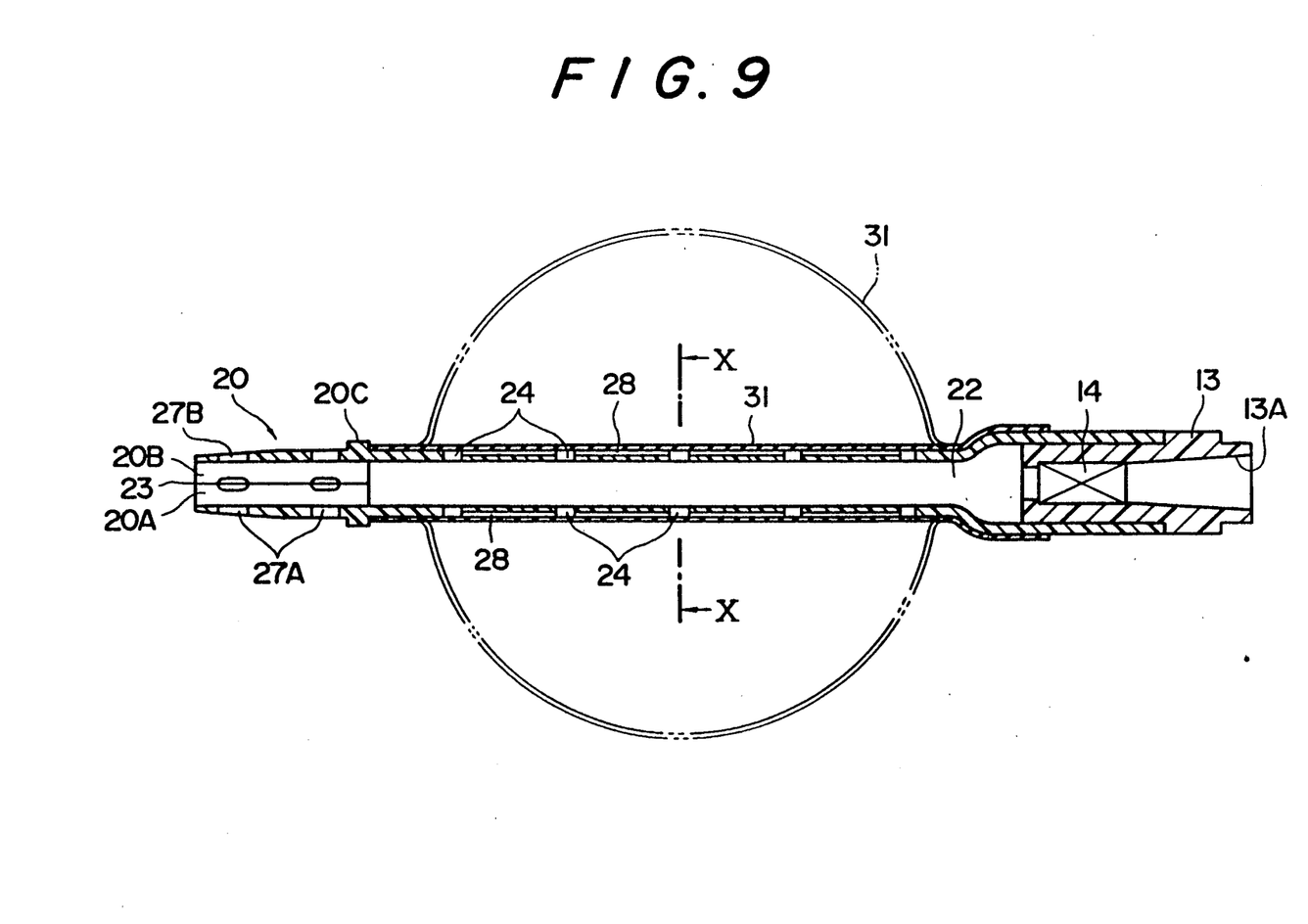
Figure 10:
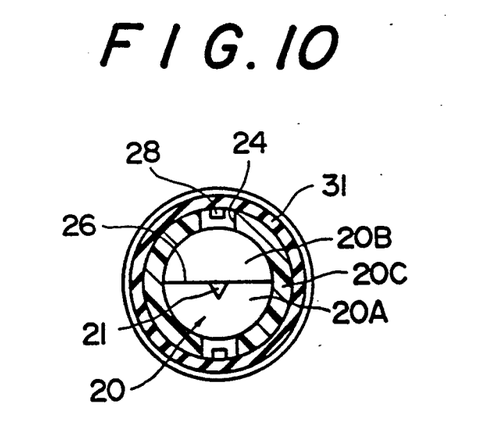
FIG. 10 is a cross-sectional view taking along the line X—X in FIG. 9.
Figure 11:
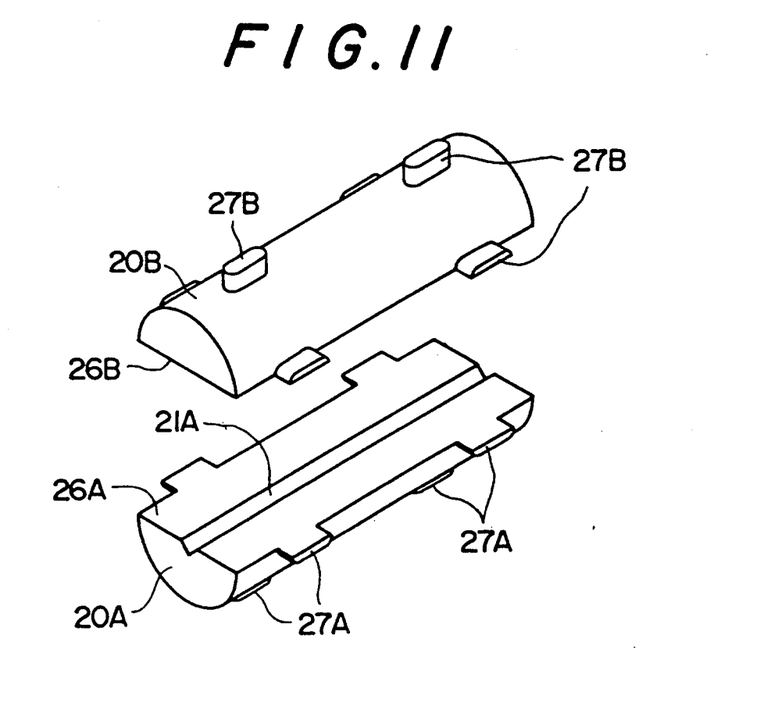
FIG. 11 is an exploded perspective view of the partial members in the embodiment shown in FIG. 9.
Figure 12:
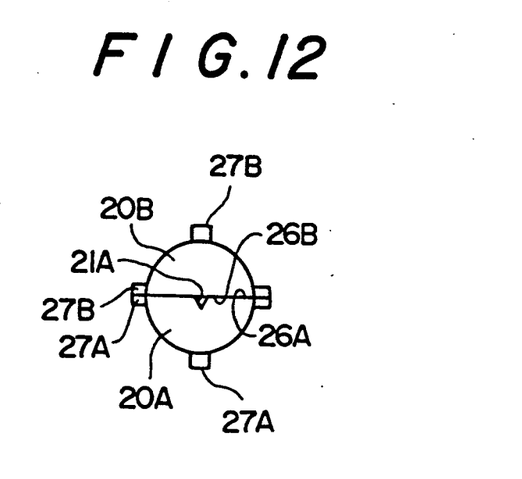
FIGS. 12 and 13 are a side view of and a front view of the joined partial members employed in the embodiment of FIG. 9.
Figure 13:
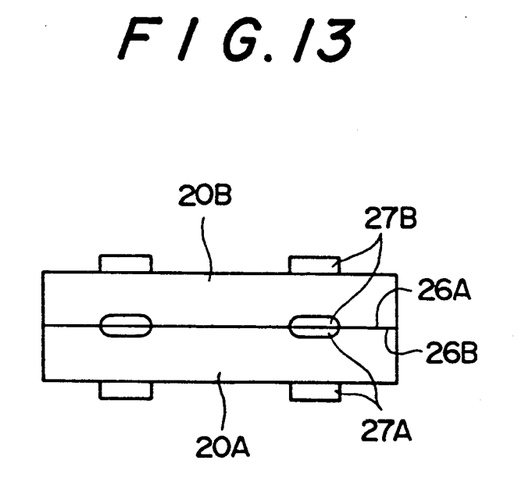

The outer periphery of each partial member 20A, 20B has such a plurality of projection 27A, 27B that can strengthen the adhesion with a resin for molding under the insert resin molding. The partial members 20A and 20B face and coincide on the joined faces 26A and 26B, and subsequently set in a cavity for injection molding. A connecting member C is so formed as to be one shape by the injection molding that it can, as shown in FIG. 9, cover the outer periphery of the partial members 20A, 20B and cylindrically extend form one end of the joined partial members 20A, 20B. The connecting member C has a plurality of communication holes 24 in its cylindrical portion and communication grooves 28 capable of communicating the communication holes 24 with one another along the axial direction.

Accordingly, the liquid outflow control unit 20 in this embodiment can be obtained by that pre-molded partial members 20A, 20B made of synthetic resin are uniformly resin-molded with the connecting member 20C.

The outer periphery of the connecting member 20C in the control unit 20 is substantially covered with the rubber-like elastic membrane 31 so as to hide on whole the communication holes 24. Fixed in the liquid receiving portion 13 is a liquid outflow prevention means 14 and mounted at a end portion 12 having a large diameter in the connecting member 20C. The interior of the large diameter of the connecting member 20C mounted on the liquid receiving portion 13 is used to be a liquid inlet 22, while at the opposite end portion of the inlet 22, a small flow control path 21 consisted of both the partial members 20A, 20B is used to be a liquid injecting portion 23.

The above-mentioned embodiment may also attain the same operations and effects as the embodiment in FIG. 1.

The connecting operation shall be easier due to uniformly molding the partial members 20A, 20B by means of the connecting member 20C. Another effect can be so expected that the liquid leakage from the joined face 26 between the tow partial members 20A and 20B.

In this embodiment of FIG. 9, the partial members 20A, 20B inserted into are not limited to be made of synthetic resin, but may be of a cut production made from the metal, a super alloy and a sintered production such as ceramics. From a practical standpoint, a resin production may be mass produced in a cheaper price, while a metal production may attain precise forming of the small path 21 to thereby control the flow amount in accurate. In the case that a resin production is employed as the partial members 20A, 20B, the material of the connecting member 20C is preferably of the same as that of the members 20A, 20B, but if the materials of both the members 20A, 20B and 20C can be welded one another, such the materials are well used.

The liquid accommodating portion 35 need not be constituted by the interiors of the expanded rubber-like membrane 31 and control unit 20. Briefly, it may be provided anywhere as long as it can accommodate a liquid and its shape is not important.

The shape of the liquid outflow control unit 20 is not limited to a cylindrical one, but may have another form, for example, of a prism or a flat. The control unit 20 need not be constituted by two substantially identical partial members as in the particular embodiment, but may be constituted by three or more partial members. In this case, a small path 21 is only required to be formed on at least one joined face 26, but may be provided on each of two or more joined faces 26. From a practical standpoint, the use of two separate partial members is advantageous for easy junction.

The liquid supply means is not limited to the syringe 12 employed in this embodiment but may be a fixed quantity delivery pump. Further, the opening/closing means is not limited to the cock 40, but may be merely a pinch which grips an elastic tube connected to the liquid injecting portion 23. Alternatively, the opening/closing means may be a regular opening/closing valve.

Furthermore, the instrument mounted on the human body is not limited to the needle 50 employed in this embodiment, but, may also be a needle with a flexible tube interposed between the mounting portion 51 and the needle edge 52, or a catheter. Suitable catheter includes a venous catheter, an ultrasonic catheter, an alimentary catheter, an obstetric catheter, a cerebral surgical catheter and so on. In the above-described embodiment, any of various type of instruments mounted on the human body is mounted on the cock 40 which is in turn mounted on the liquid injection portion 15 of the continuous liquid injector 10. However, it may also be directly mounted on the liquid injecting portion 15. In other words, it may be mounted anywhere on the side of the liquid outlet.

As has been described above, according to the present invention, accurate flow control of liquid is provided using a structure easy of mass production.

What is claim is:

1. A liquid outflow control unit adapted to be in fluid communication with a liquid supply for receiving a liquid therefrom and adapted to supply it in the manner of a continuous injector to a needle or catheter in fluid communication with said liquid supply through the outflow control unit, the control unit comprising a plurality of partial members respectively having faces extending along a direction of flow of liquid through the unit and which faces are joined together so that the partial members form the unit, at least one of the partial members having a path means extending along its said face for forming at least a part of a small flow control path through said members when said faces are joined, said control path having one end terminating in a liquid outlet which is adapted to communicate with said needle or catheter, said at least a part of said control path having a predetermined length and a predetermined cross-sectional dimension to control the flow rate of liquid through the unit, wherein said control unit further includes a plurality of communication holes providing communication between said liquid inlet in the small flow control path and the outer surface of the liquid outflow control unit defined by outer surfaces of said partial members, wherein said path means includes a groove formed between the joined faces of the partial members and extending in a zigzag manner along said faces between the liquid inlet and the liquid outlet, further including an elastic membrane provided so as to cover the outer surfaces of the partial members for accommodating liquid within the elastic membrane, whereby expansion of the membrane by fluid exerts a fluid pressure to inject fluid through the control path.

2. A liquid outflow control unit according to claim 1, wherein the small flow control path includes a groove formed on the joined face of one partial member and another said partial member has a flat, ungrooved face adapted to join with the joined face of said one partial member to define said control path therebetween.

3. A liquid outflow unit according to claim 1, wherein the small flow control path is defined by grooves respectively formed in the joined faces of said partial members for mating engagement with each other.

4. A liquid outflow control unit according to claim 1, further including liquid leakage prevention means provided around the small flow control path for preventing leakage from the path, said liquid leakage prevention means including a rib formed on one said partial member and a groove formed in another said partial member which groove is complementary in shape to the rib.

* * * * *